United States Patent
Miller et al.

(10) Patent No.: US 9,895,676 B2
(45) Date of Patent: Feb. 20, 2018

(54) PROCESSES AND CATALYSTS FOR CONVERTING ALKANES TO ALKENES

(71) Applicant: Sajet Development LLC, Houston, TX (US)

(72) Inventors: Jorge Miller, Houston, TX (US); Luisa Kling Miller, Houston, TX (US); Barry L. Stucky, Houston, TX (US)

(73) Assignee: Sajet Development LLC, Houston, TX (US)

( * ) Notice: Subject to any disclaimer, the term of this patent is extended or adjusted under 35 U.S.C. 154(b) by 444 days.

(21) Appl. No.: 14/398,891

(22) PCT Filed: May 6, 2013

(86) PCT No.: PCT/US2013/039714
§ 371 (c)(1),
(2) Date: Nov. 4, 2014

(87) PCT Pub. No.: WO2013/173104
PCT Pub. Date: Nov. 21, 2013

(65) Prior Publication Data
US 2015/0119621 A1 Apr. 30, 2015

Related U.S. Application Data

(60) Provisional application No. 61/648,185, filed on May 17, 2012.

(51) Int. Cl.
*B01J 21/16* (2006.01)
*B01J 8/08* (2006.01)
(Continued)

(52) U.S. Cl.
CPC .............. *B01J 21/16* (2013.01); *B01J 8/085* (2013.01); *B01J 8/125* (2013.01); *B01J 8/1809* (2013.01); *B01J 23/02* (2013.01); *B01J 23/06* (2013.01); *B01J 23/92* (2013.01); *B01J 29/082* (2013.01); *B01J 29/90* (2013.01); *B01J 35/002* (2013.01);
(Continued)

(58) Field of Classification Search
CPC ... B01J 21/16; B01J 23/02; B01J 23/06; B01J 35/0086
USPC .......... 502/80, 84, 170, 340; 428/403; 264/7, 264/15, 642, 679, 681
See application file for complete search history.

(56) References Cited

U.S. PATENT DOCUMENTS 3,553,104 A * 1/1971 Stover et al. ............ B01J 21/16
208/120.1
4,378,308 A * 3/1983 Angevine ................ B01J 23/85
208/213

(Continued)

OTHER PUBLICATIONS

International Search Report and Written Opinion for PCT/US2013/039714 dated Aug. 30, 2013.

*Primary Examiner* — Patricia L. Hailey
(74) *Attorney, Agent, or Firm* — Vorys, Sater, Seymour and Pease LLP

(57) ABSTRACT

Generally, regenerable, encapsulated metal oxide catalysts comprising a ceramic matrix and metal catalysts may be used to convert alkanes to alkenes. The encapsulated metal oxide catalyst may be tailored to produce a variety of alkenes including ethylene, butylene, and propylene. Further, the encapsulated metal oxide catalysts advantageously allow for regeneration and reactant recovery for cost effective and environmentally friendly processes.

21 Claims, 4 Drawing Sheets

(51) Int. Cl.
| | |
|---|---|
| *B01J 8/12* | (2006.01) |
| *B01J 8/18* | (2006.01) |
| *C07C 1/26* | (2006.01) |
| *B01J 37/04* | (2006.01) |
| *B01J 23/02* | (2006.01) |
| *B01J 29/08* | (2006.01) |
| *B01J 35/00* | (2006.01) |
| *B01J 35/02* | (2006.01) |
| *B01J 35/10* | (2006.01) |
| *B01J 37/00* | (2006.01) |
| *B01J 37/14* | (2006.01) |
| *C07C 1/30* | (2006.01) |
| *B01J 37/06* | (2006.01) |
| *B01J 37/08* | (2006.01) |
| *B01J 38/30* | (2006.01) |
| *B01J 23/06* | (2006.01) |
| *B01J 23/92* | (2006.01) |
| *B01J 29/90* | (2006.01) |
| *B01J 35/08* | (2006.01) |

(52) U.S. Cl.
CPC ....... *B01J 35/0006* (2013.01); *B01J 35/0093* (2013.01); *B01J 35/023* (2013.01); *B01J 35/026* (2013.01); *B01J 35/08* (2013.01); *B01J 35/1061* (2013.01); *B01J 35/1066* (2013.01); *B01J 37/0009* (2013.01); *B01J 37/0018* (2013.01); *B01J 37/0063* (2013.01); *B01J 37/0072* (2013.01); *B01J 37/04* (2013.01); *B01J 37/06* (2013.01); *B01J 37/086* (2013.01); *B01J 37/088* (2013.01); *B01J 37/14* (2013.01); *B01J 38/30* (2013.01); *C07C 1/26* (2013.01); *C07C 1/30* (2013.01); *B01J 2208/00274* (2013.01); *C07C 2521/10* (2013.01); *C07C 2521/16* (2013.01); *C07C 2527/232* (2013.01); *Y02P 20/584* (2015.11)

(56) References Cited

U.S. PATENT DOCUMENTS

| | | | |
|---|---|---|---|
| 4,568,448 A * | 2/1986 | Angevine | B01J 23/85 208/213 |
| 5,302,773 A * | 4/1994 | Vrieland | B01J 23/28 502/254 |
| 5,527,979 A | 6/1996 | Agaskar et al. | |
| 6,180,559 B1 * | 1/2001 | Roberts | B01J 23/02 423/608 |
| 7,476,637 B1 * | 1/2009 | Boyer | B01J 29/06 502/60 |
| 2003/0069452 A1 | 4/2003 | Sherman et al. | |
| 2006/0183942 A1 | 8/2006 | Gaffney et al. | |
| 2010/0087688 A1 * | 4/2010 | Miller | B01J 21/16 568/891 |

\* cited by examiner

PROCESSES AND CATALYSTS FOR CONVERTING ALKANES TO ALKENES

CROSS-REFERENCE TO RELATED APPLICATIONS

The present application claims priority to U.S. Provisional Patent Application No. 61/648,185 filed on May 17, 2012, entitled "Process and Catalysts for Converting Alkanes to Alkenes," the entire disclosure of which is incorporated herein by reference.

BACKGROUND

The present invention relates to methods and catalysts for producing alkenes from alkanes. More particularly, the present invention relates to regenerable, encapsulated metal oxide catalysts and cost-effective processes utilizing such catalysts to convert alkanes to alcohols then to alkenes.

Lower alkenes, such as ethylene, propylene, and butylene, are used for a variety of applications. For example, ethylene is one of the most produced organic compounds in the world, with the majority of ethylene being used to produce ethylene oxide, ethylene dichloride, and polyethylene. Lower alkenes may be recovered from petroleum by fractional distillation, however, demand far exceeds recovery by this method. Therefore, the majority of lower alkenes are produced by energy intensive and expensive cracking processes that are well-known in the art. For example, ethylene is commonly produced at about 700-950° C. in the presence of steam followed by rapid cooling, thereby "cracking" large hydrocarbons into smaller ones and introducing unsaturation. Ethylene may then be separated from the resulting product mixture by repeated compression and distillation processes. Common drawbacks of the steam-cracking processes can include environmental issues, like $CO_2$ and $NO_x$ production, and its energy-intensive nature, which results in a high-cost process. Further, alternative methods used in place of steam-cracking, including fluidized bed catalytic process, have their own limitations and drawbacks.

Other methods are known for producing alkenes, e.g., acid dehydration of alcohols. Generally, acid dehydration of alcohols proceeds by reaction of alkyl halides and metal hydroxides. Such methods, however, have heretofore, not been commercially viable. The primary hindrances to commercial scale-up of these methods include catalyst attrition and over-halogenation problems, which result in the need for expensive re-crystallation.

Among other things, a need remains unaddressed for a process to form alkenes in commercially viable processes, with a minimization or elimination of undesirable byproducts including higher halides.

SUMMARY OF THE PRESENT INVENTION

The present invention relates to methods and catalysts for producing alkenes from alkanes. More particularly, the present invention relates to regenerable, encapsulated metal oxide catalysts and cost-effective processes utilizing such catalysts to convert alkanes to alcohols and/or ethers to alkenes.

In one embodiment of the present invention, an encapsulated metal oxide catalyst presented herein may comprise a porous ceramic matrix and a metal oxide encapsulated therein, wherein the encapsulated metal oxide catalyst has a crush strength of about 10,000 psi or greater.

In one embodiment of the present invention, an encapsulated metal oxide catalyst presented herein may comprise a porous ceramic matrix and a metal oxide encapsulated therein, wherein the encapsulated metal oxide catalyst has a void volume of about 25% to about 85%.

In yet another embodiment of the present invention, a method presented herein may comprise producing a dough of a clay, a metal salt, and water; forming a pellet from the dough; drying the pellet; calcining the pellet so as to form an encapsulated metal oxide catalyst comprising a porous ceramic matrix and a metal oxide encapsulated therein; and washing the encapsulated metal oxide catalyst with a water miscible solvent.

In another embodiment of the present invention, a process presented herein may comprise producing an alkene from an alkyl halide in the presence of an encapsulated metal oxide catalyst, the encapsulated metal oxide catalyst comprising a porous ceramic matrix and a metal catalyst encapsulated therein such that in the production of the alkene the metal catalyst converts from a metal oxide to a metal halide; regenerating the encapsulated metal oxide catalyst by converting the metal halide to the metal oxide in an oxygen-rich gas so as to produce an effluent comprising a halogen gas; recovering at least 90% of the halogen gas from the effluent; reacting the halogen gas with an alkane to produce a second alkyl halide; and producing a second alkene from the second alkyl halide.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present invention relates to methods and catalysts for producing alkenes from alkanes. More particularly, the present invention relates to regenerable, encapsulated metal oxide catalysts and cost-effective processes utilizing such catalysts to convert alkanes to alcohols and/or ethers to alkenes.

The present invention provides for, in some embodiments, processes for the production of alkenes on an industrial scale due, at least in part, to an ability to regenerate the catalyst, an ability to capture and reuse halogen gases, a reduced cost of system materials as a result of improved encapsulated metal oxide catalysts, and reduced energy requirements of the process as compared to other alkene production processes.

The present invention provides for, in some embodiments, encapsulated metal oxide catalysts capable of converting alkanes to alcohols and then the alcohols to alkenes, wherein the encapsulated metal oxide catalysts are at least substantially regenerated in the process.

As used herein, the term "encapsulated metal oxide catalyst" refers to a porous ceramic matrix having metal catalysts dispersed and substantially immobilized therein as described herein. It should be noted that "encapsulated" does not necessarily refer to individual metal catalysts being 100% sheathed by the porous ceramic matrix. As described herein, in some embodiments, encapsulated metal oxide catalysts of the present invention comprise at least two catalytic components, e.g., (1) metal catalysts for the conversion of alkyl halides to alcohols and (2) the porous ceramic matrix for the conversion of alcohols to alkenes.

As used herein, the term "metal catalyst" refers to a metal compound of the encapsulated metal oxide catalyst. As described herein, the metal catalyst is converted between the metal halide and metal oxide forms. It should be noted that the metal oxide form of the metal catalyst includes oxidized metals in chemical forms like $MO_x$, $M(OH)_x$, or any hybrid thereof. Further, the metal compound may be in more than one configuration, such as, individual metal compounds (e.g., an individual $Mg(OH)_2$), clusters of 3-10 metal compounds, and/or small particles of a plurality of metal compounds.

Figure 1:
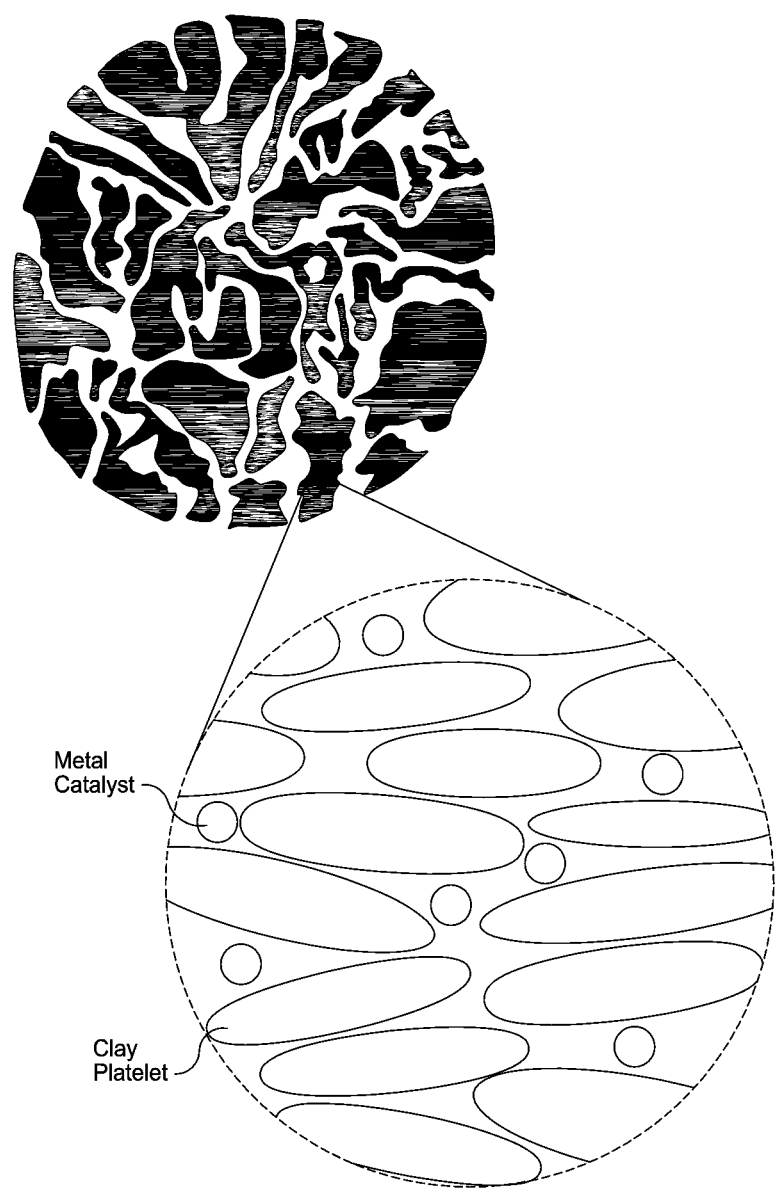
FIG. 1 is an illustration of an encapsulated metal oxide catalyst according to some embodiments of the present invention.

FIG. 1 provides a nonlimiting illustration of an encapsulated metal oxide catalyst according to some embodiments of the present invention. Generally, the metal catalysts are disposed between clay platelets. The pores of the ceramic matrix and spacing between the clay platelets provide the gaseous reactants access to the metal catalysts. Further, the metal catalysts may be associated with the clay platelets to varying degrees, e.g., completely, substantially, or partially surrounded by clay platelets.

In at least some embodiments, it is believed that the ceramic matrix may advantageously provide (1) a porous structure that allows reactants to access the metal catalysts, (2) a robust structure that provides unique processing capabilities, and (3) an uncomplicated structure with straightforward production methods that minimizes the cost of the encapsulated metal oxide catalysts.

The processes of the present invention for converting alkanes to alkenes, in some embodiments, utilize a halogen gas, e.g., chlorine and/or bromine, in an initial chemical reaction and produce the same halogen gas in a subsequent chemical reaction, thereby providing for recapturing and reuse of the halogen gas. Reuse of the halogen gas may reduce the overall cost associated with the expensive halogen gas, reduce worker handling of halogenated chemicals, and minimize halogenated waste.

However, as a consequence of utilizing a halogen gas, systems for the production of alkenes from alkanes often require expensive reaction vessels because halogen gases at elevated temperatures will react with a plurality of metals. For example, tube reactors may need to be formed from an INCONEL® material (an austenitic nickel-chromium-based superalloy, available from Special Metals Corporation), which is one of the most expensive materials and can account for a large portion of the cost of the system.

However, as described herein a cost-saving synergy has been found through controlling the reaction conditions to take advantage of a previously unrealized smaller pore size of the encapsulated metal oxide catalysts. That is, by controlling the reaction conditions and hindering the metal catalysts from forming fully hydrated compositions, the pore sizes of the encapsulated metal oxide catalysts can be advantageously reduced, perhaps by more than 5 times. Pore size reduction proportionally reduces the encapsulated metal oxide catalyst volume, which consequently reduces the size of the reactor (and thus the amount of INCONEL® or other expensive reactor material). In some embodiments, encapsulated metal oxide catalysts of the present invention may be designed such that the size of the system may be reduced by at least half, thereby translating to significant cost savings and easier scale-up and commercialization.

It should be noted that when "about" is provided at the beginning of a numerical list, "about" modifies each number of the numerical list. It should be noted that in some numerical listings of ranges, some lower limits listed may be greater than some upper limits listed. One skilled in the art will recognize that the selected subset will require the selection of an upper limit in excess of the selected lower limit.

I. Encapsulated Metal Oxide Catalysts of the Present Invention

Generally, it is believed that converting alkanes to alkenes according to at least some embodiments of the present invention proceeds via three basic chemical processes: (1) halogenation and (2) alcohol formation with immediate (3) alkene formation. Advantageously, the encapsulated metal oxide catalysts of the present invention may be regenerated by a fourth chemical process, i.e., (4) catalyst regeneration and halogen gas production.

By way of nonlimiting example, the following reactions illustrate the conversion of methane to ethylene utilizing bromine and a magnesium-based metal catalyst.

Bromination

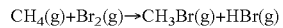
$$CH_4(g)+Br_2(g)\rightarrow CH_3Br(g)+HBr(g)$$

Alcohol Formation

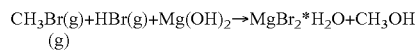
$$CH_3Br(g)+HBr(g)+Mg(OH)_2\rightarrow MgBr_2*H_2O+CH_3OH(g)$$

Alkene Formation

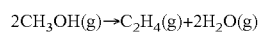
$$2CH_3OH(g)\rightarrow C_2H_4(g)+2H_2O(g)$$

Catalyst Regeneration and Halogen Gas Production

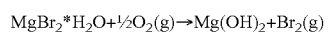
$$MgBr_2*H_2O+\tfrac{1}{2}O_2(g)\rightarrow Mg(OH)_2+Br_2(g)$$

As previously discussed, processes utilizing these reaction steps have heretofore been commercially impracticable because of, inter alia, attrition of the catalysts used in the processes and significant expense. However, it is believed that at least in some embodiments of the present invention, the encapsulated metal oxide catalysts provided herein mitigate metal catalyst attrition during the production of alkenes from alkanes.

In some embodiments, encapsulated metal oxide catalysts of the present invention may be produced by creating a dry mix of, at least, (1) one or more insoluble or slightly soluble metal salts, (2) one or more clay materials, and (3) optional additives, where each solid component is preferably a fine powder. Then water is added slowly to the dry mix to create a dough that is just wet enough for forming pellets. Pellets formed from the dough may then be dried, preferably naturally, i.e., without added heat. The dried pellets may then be calcined to between about 600° C. and about 1000°

C. in an oxygen-containing gas stream, e.g., air or $O_2$ in an inert carrier gas, to form encapsulated metal oxide catalysts.

Suitable metal salts for use in conjunction with forming encapsulated metal oxide catalysts may include, but are not limited to, a salt (hydrated or otherwise) of a $C_1$-$C_{16}$ comprising at least one carboxylate (e.g., carbonate, oxalate, lactate, citrate, stearate, and the like) and any alkali, basic, or transition metal, and most preferably, magnesium or zinc. As described below, generally, the metal salt may be chosen based on the molecular volume of the salt so as to create a desired pore size that contains the metal oxide after calcining. In preferred embodiments, magnesium carbonate trihydrate may be used in forming encapsulated metal oxide catalysts of the present invention.

In some embodiments, the metal salts may be included in the dough such that the metal concentration (i.e., Mg or Zn concentration) ranges from a lower limit of about 5%, 10%, or 25% by weight of the dry clay material to an upper limit of about 50%, 40%, or 35% by weight of the dry clay material, and wherein the metal concentration may range from any lower limit to any upper limit and encompass any subset therebetween. It should be noted that the term "dry clay material" refers to an as-received clay material with any intrinsic hydration.

Suitable clay materials for use in conjunction with forming encapsulated metal oxide catalysts of the present invention may include, but are not limited to, pozzalonic materials, kaolin, metakaolin, bentonite, bauxite, illite, vermiculite, Fuller's earth, hectorite, saponite, speiolite, shale, halloysite, pumice, pumicite, montmonillonite, chlorite clays, certain phylosilicates, mica, or any combination thereof.

Suitable additives for use in conjunction with forming encapsulated metal oxide catalysts of the present invention may include, but are not limited to, activation agents, pore molding agents, or any combination thereof.

As described in more detail below, suitable activation agents are compositions that catalyze alkene formation. Generally, activation agents are used in conjunction with clay materials that themselves are not efficient at catalyzing the alkene formation. However, activation agents may be used in conjunction with clay materials that efficiently catalyze alkene formation. Suitable activation agents for use in conjunction with forming encapsulated metal oxide catalysts of the present invention may include, but are not limited to, X-type zeolites in an acid form, Y-type zeolites, silica powders, analcime, chabazite, clinoptilolite, heulandite, natrolite, phillipsite, stilbite, or any combination thereof.

In some embodiments, activation agents may be included in the dough in an amount ranging from a lower limit of about 5%, 15%, 25%, or 50% by weight of the dry clay material to about 100%, 80%, 75%, or 65% by weight of the dry clay material, and wherein the activation agent concentration may range from any lower limit to any upper limit and encompass any subset therebetween.

As used herein, the term "pore molding agents" refers to a water soluble molecule or compound used as a template for pores not housing metal catalysts that will generally decompose with minimal residue during the calcining process. Without being limited by theory, it is believed that when incorporated in the dough some of the pore molding agents will reside between clay platelets. When dried, the pore molding agents restrict the distance between clay platelets. During calcining, the pore molding agents decomposed with minimal residue leaving a pore between clay platelets of a desired size. As described below, the pore size between platelets may act to restrict the size of the alkene produced, which may advantageously minimize higher molecular weight byproducts that are present in other alkene production methods.

Generally, pore molding agents are small organic molecules or compounds with a size and confirmation similar to the alkene of interest. Without being limited by theory, it is believed that the pores not housing metal catalysts may act as templates in the alkene formation reaction in that the pores limit the size of the alkene formed. Suitable pore molding agents for use in conjunction with forming encapsulated metal oxide catalysts of the present invention may include, but are not limited to, glycol, diethylene glycol, glycerin, oligomers of ethylene glycol, malonic acid, succinic acid, and the like, or any combination thereof.

In some embodiments, pore molding agents may be included in the dough in an amount ranging from a lower limit of about 1%, 5%, 10%, or 20% by weight of the dry clay material to about 50%, 40%, 30%, or 25% by weight of the dry clay material, and wherein the pore molding agent concentration may range from any lower limit to any upper limit and encompass any subset therebetween.

Water, preferably distilled or deionized water to mitigate contamination, may be included in the dough so that the dough can be worked with and formed into pellets. Most preferably, the amount of water used is an amount sufficient to form the dough into a desired shape like a pellet. One skilled in the art should understand that the amount of water may depend on, among other things, the clay materials and the method of forming the pellets or other shape. In some embodiments, water may be included in the dough in an amount ranging from a lower limit of about 10%, 15%, or 20% by weight of the dry clay material to about 50%, 40%, or 30% by weight of the dry clay material, and wherein the water concentration may range from any lower limit to any upper limit and encompass any subset therebetween.

By way of a nonlimiting example, encapsulated metal oxide catalysts may be formed from a dough comprising bentonite (100 parts by weight), magnesium carbonate trihydrate (33 parts calculated by weight of magnesium), and water (18 parts by weight). By way of another nonlimiting example, encapsulated metal oxide catalysts described herein may be formed from a dough comprising kaolin (100 parts by weight), X-type zeolite (25 parts by weight), magnesium carbonate tri-hydrate (27 parts by weight of magnesium), and water (22 parts by weight).

Without being bound to any particular theory at this time, it is believed that the platelets of the clay material are coordinated by the metal ions of the metal salt, which may assist in the formation of the pore in which the metal catalyst resides. The chemical composition of the clay and the volume of counter ions in the organic salt may, at least in part, account for the pore size in the final ceramic matrix of the encapsulated metal oxide catalyst. A properly sized pore for containing the metal catalyst may be important for maintaining the integrity of the ceramic matrix because as the metal catalyst therein changes chemical composition, e.g., between the halide and the oxide forms, the size of the metal catalyst may change. Accordingly, a ceramic matrix with a pore size too small may crack when the metal catalyst expands, and a ceramic matrix with a pore size too large may have a reduced physical strength and an unnecessarily large volume, which increases the size of the system and consequently the amount of expensive reactor materials (e.g., INCONEL®) that provide chemical compatibility with heated halogen gases during some of the reactions.

By way of nonlimiting example, if magnesium citrate, having a molar volume of about 460 cubic centimeters per mole, is used as the metal salt, the pores left in the encapsulated metal oxide catalysts formed from the mixture would be sufficient to accommodate the maximum size of the magnesium chloride hexa-hydrate, which is 130 cubic centimeters per mole.

In some embodiments, the conditions of each of the reactions may be controlled, as described below, to prevent full hydration of the metal catalyst at various points in the reaction, thereby allowing for smaller pore sizes and more compact and robust encapsulated metal oxide catalysts. By way of nonlimiting example, if magnesium carbonate trihydrate, having a molar volume of about 74, is used as the metal salt, the pores left in the encapsulated metal oxide catalysts formed from the mixture would not be sufficient to accommodate the maximum size of the magnesium chloride hydrate, which is 130 cubic centimeters per mole for the hexa-hydrate $MgCl_2*6H_2O$. Accordingly, the reaction conditions may be controlled to prevent the formation of a metal catalyst of fully hydrated magnesium chloride (or bromide).

The pellets can be made spherical or in any other shape, by hand or by machine techniques, known in the art. By way of nonlimiting example, pellets may be generally cylindrical and have a diameter of about 4 mm and a length of about 6 mm. By way of another nonlimiting example, pellets may have a substantially spherical to ovular shape with the largest diameter dimension ranging from about 2 mm to about 10 mm. One skilled in the art, with the benefit of this disclosure should understand the plurality of shapes and sizes that can be formed with a dough comprising clay materials. For example, sheet, ribbons, or strands may be formed if desired.

After drying, the pellets may be calcined in an oxygen-rich environment to form the encapsulated metal oxide catalysts. Because the pellets may still contain an appreciable amount of water, generally, the temperature during calcining may advantageously be ramped up slowly, and optionally have intermediate plateau or hold temperatures, because quickly removing water from the pellets can cause the walls of the pores (both with and without metal catalyst) to crack, which reduces structural integrity and increases attrition.

In some embodiments, encapsulated metal oxide catalysts may comprise a plurality of pores containing metal catalysts having an average diameter ranging from a lower limit of about 5 nm, 10 nm, 25 nm, or 50 nm to an upper limit of about 300 nm, 250 nm, 200 nm, or 100 nm, and wherein the average diameter may range from any lower limit to any upper limit and encompass any subset therebetween. By way of nonlimiting example, encapsulated metal oxide catalysts may comprise a plurality of pores containing metal catalysts having an average diameter of about 10 nm to about 100 nm.

In some embodiments, encapsulated metal oxide catalysts may comprise a plurality of pores between clay platelets having an average diameter ranging from a lower limit of about 2 nm, 5 nm, or 10 nm to an upper limit of about 50 nm, 40 nm, or 30 nm, and wherein the average diameter may range from any lower limit to any upper limit and encompass any subset therebetween.

In some embodiments, encapsulated metal oxide catalysts may have a void volume ranging from a lower limit of about 25%, 35%, or 50% to an upper limit of about 85%, 75%, or 60%, and wherein the void volume may range from any lower limit to any upper limit and encompass any subset therebetween.

In some embodiments after calcining, the encapsulated metal oxide catalysts may be washed with a water miscible organic solvent, e.g., acetone, alcohol (e.g., methanol, ethanol, or propanol), or the like. Washing with a water miscible organic solvent may advantageously increase the crush strength of the encapsulated metal oxide catalysts.

By way of a nonlimiting example, encapsulated metal oxide catalysts formed from a dough comprising bentonite, magnesium carbonate, and water may be washed with water and methanol after calcining.

In some embodiments, after calcining, encapsulated metal oxide catalysts may have a crush strength of about 10,000 psi or greater, more preferably about 25,000 psi or greater, and most preferably about 60,000 psi or greater.

II. Processes of the Present Invention

As shown above, processes for converting alkanes to alkenes and catalyst regeneration according to at least some embodiments of the present invention involve the processes of (1) halogenation, (2) alcohol formation with immediate (3) alkene formation, and (4) catalyst regeneration and halogen gas production.

Halogenation involves reacting an alkane and a halogen gas to form an alkyl halide. In some embodiments, alkyl halides may be provided rather than produced directly in the systems and/or processes of the present invention. By way of nonlimiting example, methyl bromide may be produced at a first location and then transported to a system of the present invention for further reaction.

Alkanes suitable for use in conjunction with the present invention may include, but are not limited to, any alkanes or mixtures thereof with at least one alkane having one or more carbon atoms, e.g., methane, ethane, propane, butane, pentane, hexane, and so one, or any combination thereof. In preferred embodiments, the alkane may be substantially methane.

Halogen gases for use in conjunction with the present invention may include, but are not limited to, fluorine, chlorine, bromine, iodine, or any combination thereof. In preferred embodiments, the halogen gas may be bromine.

Halogenation of an alkane may be accomplished by any of a number of reactions, including catalyzed reactions, known in the art. In some embodiments, alkane halogenation may involve the use of ultraviolet light and/or heat to catalyze the reaction. In some embodiments, when temperature is used as a catalyst for the halogenation reaction, the temperature may range from 100° C. and 500° C., more preferably from 150° C. to 400° C., and most preferably from 250° C. to 350° C.

In some embodiments, the mole ratio of alkane to halogen gas may range from about 10:1 to about 1:1, or more preferably about 5:1 to about 1:1.

After production of an alkyl halide, or in some embodiments providing an alkyl halide, the alkyl halide may be brought into contact with encapsulated metal oxide catalysts of the present invention (according to any embodiment described herein) at an elevated temperature so as to yield an alcohol that is then converted to an alkene. That is, the alkyl halide may react with the metal catalyst in its metal oxide form to yield an alcohol and a metal halide, and the alcohol may then react with the ceramic matrix and/or activation agents to form the alkene. The lifetime of the alcohol may be very short, e.g., almost immediate conversion to the alkene.

In some embodiments, the temperature for the alcohol formation and alkene formation is preferably between about 350° C. and about 400° C., but temperatures as low as about 100° C. and as high as about 425° C. may be utilized.

In some embodiments, the conditions for the alcohol formation with immediate alkene formation may be tailored such that the metal catalyst of the encapsulated metal oxide catalyst converts to a metal halide with minimal waters of hydration so as to prevent cracking of the porous ceramic matrix. For example, when employing encapsulated metal oxide catalysts having smaller pore sizes, e.g., less than about 200 molar volume, excess waters of hydration on the metal halide cause the metal halide to grow beyond 200 molar volume, thereby exceeding the pore size and causing the walls of the encapsulated metal oxide catalyst to crack. When cracking of the porous ceramic matrix is extensive enough, the encapsulated metal oxide catalysts may crumble and fall apart, which in some processes and apparatuses may lead to plugging and encapsulated metal oxide catalyst attrition.

Alkenes that may be produced from this process may include, but are not limited to, ethylene, propene, butene, pentene, hexene, and the like, or any combination thereof. In some embodiments, the alkene product may be a mixture of alkenes.

In some embodiments, the pores between clay platelets may be advantageously sized to direct the alcohol to alkene reaction to predominantly produce a desired alkene. By way of nonlimiting example, the use of a glycerin pore molding agent in the formation of encapsulated metal oxide catalysts may allow pores to form between clay platelets that are sized appropriately to preferentially form butylene products in the alkene reaction.

One skilled in the art with the benefit of this disclosure should understand that a particular alkene produced will depend on, inter alia, the alkane feed gas, the metal catalyst of the encapsulated metal oxide catalysts, the structure of the ceramic matrix of the encapsulated metal oxide catalysts (e.g., the various pore sizes, void volume, surface area, etc.), the presence of additives such as pore molding agents in the manufacturing of encapsulated metal oxide catalysts, the composition of the ceramic matrix (or activation agents) of the encapsulated metal oxide catalysts, and the reaction temperature.

After the metal catalyst is in the form of a metal halide, the encapsulated metal oxide catalyst may be treated within oxygen-rich gas at an elevated temperature to regenerate the metal halide form of the metal catalyst back to a metal oxide form. Suitable oxygen-rich gases may include, but are not limited to, air, oxygen in an inert carrier gas, or any combination thereof. Suitable temperatures for metal catalyst recovery may range from about 300° C. to about 800° C., more preferably about 350° C. to about 475° C., and most preferably about 375° C. to about 425° C.

A product of the regeneration reaction is halogen gas (an expensive reactant in the halogenation reaction), which is preferably recovered for reuse with fresh alkane. Because halogen gas is only a portion of the effluent after the catalyst regeneration reaction, additional processing steps may be used to extract the halogen gas from the mixture of gases. Suitable processing steps to extract and purify the halogen gas may include, but are not limited to, condensing, stripping, compressing, desiccating (to dry a gas mixture), distilling, and other suitable processes.

In some embodiments, the halogen gas produced during catalyst regeneration may be recovered by condensing a substantial portion of the halogen gas from the effluent of the catalyst regeneration reaction followed by dry methods (i.e., water-free methods) to extract the remaining halogen gas. Dry methods may advantageously mitigate water contamination of the halogen gas, which may be present in stripper methods. Because the various reactions described herein are preferably preformed with substantially dry gases, water contamination may require additional purification steps including passing the gases over desiccants.

In some embodiments, a process of the present invention may recycle preferably at least about 90% of the halogen gas, more preferably at least about 94%, or most preferably at least about 99%.

III. Systems for Performing Processes of the Present Invention

Figure 2:
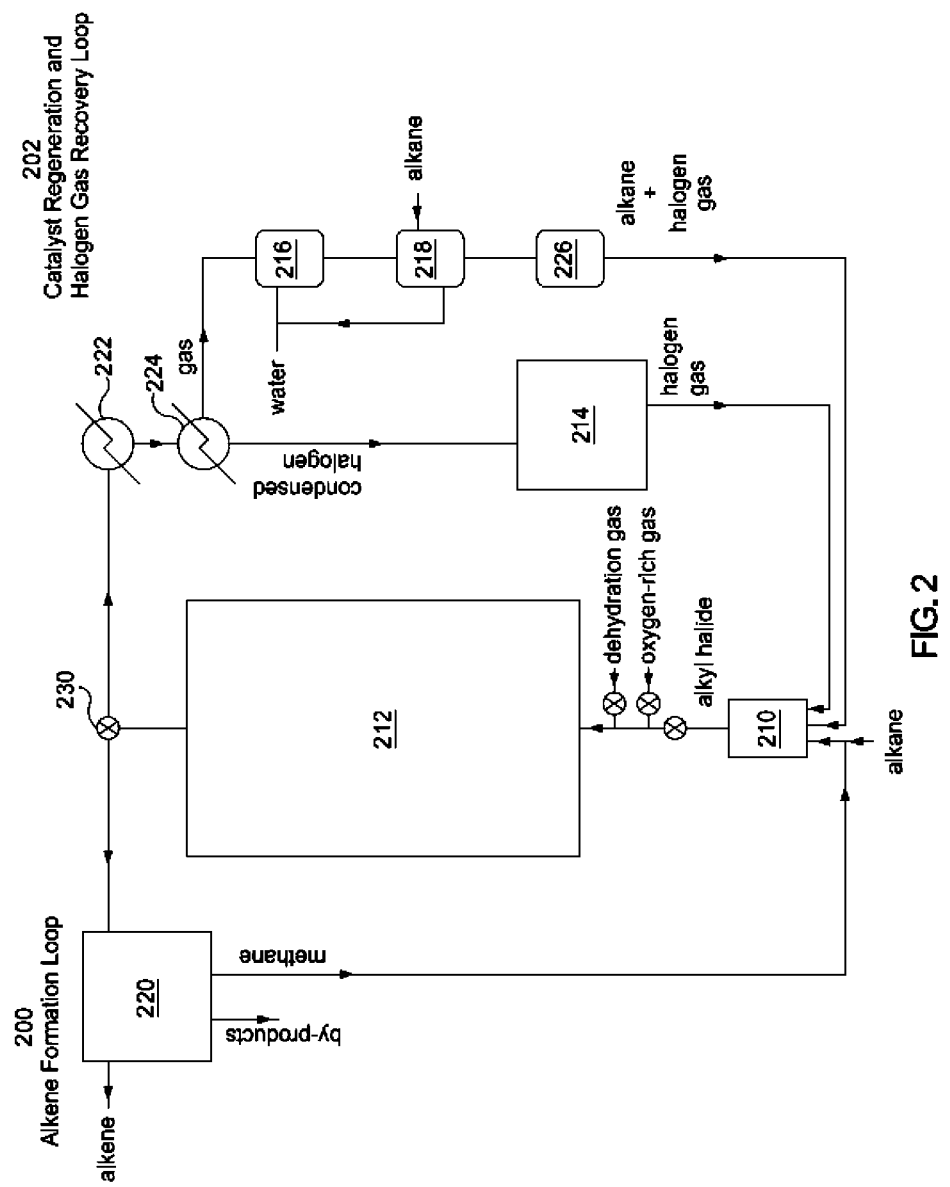
FIG. 2 is a schematic diagram of a nonlimiting example of a system of the present invention for producing alkenes according to some embodiments of the processes of the present invention.

Referring now to FIG. 2, processes of the present invention may, in some embodiments, be performed with the nonlimiting example of materials flow and equipment schematically illustrated. Generally, a system with encapsulated metal oxide catalysts (according to any embodiment described herein) housed in reactor 212 may be associated with two loops that run alternatively. One loop may be an "Alkene Formation Loop" 200 wherein the reactions in reactor 212 are alcohol formation, alkene formation, and the metal catalyst converts from metal oxide to metal halide. The second loop may be a "Catalyst Regeneration and Halogen Gas Recovery Loop" 202 wherein the metal catalysts convert from metal halide to metal oxide and halogen gas is produced.

As shown in FIG. 2, alkane and halogen gases are introduced into halogenation reactor 210 to form an alkyl halide, which then flows to reactor 212, e.g., a tubular reactor, a Johnson screen reactor, a fluidized bed reactor, or the like. It should be noted that the dehydration gas and oxygen-rich gas are closed from reactor 212 when alkyl halide is being introduced into reactor 212. The reaction effluent from reactor 212, i.e., a gas mixture comprising alkene, byproducts, and unreacted gases, is then directed toward purifier 220 with valve 230. Purifier 220 may comprise a plurality of apparatuses to achieve alkene purification, e.g., demethanizers, condensers, desiccators, compressors, distillers, diffusion process equipment, and the like. After purifier 220, the alkene may be collected, and methane may be recirculated to halogenation reactor 210.

To regenerate the metal catalysts of the encapsulated metal oxide catalysts of the present invention, oxygen-rich gas may be introduced into reactor 212. Generally, the dehydration gas and alkyl halide gas are closed from reactor 212 when the oxygen-rich gas is being introduced into reactor 212. The regeneration effluent from reactor 212, which comprises a gas mixture including halogen gas and unreacted oxygen-rich gas, is then directed toward condensers 222 and 224 with valve 230. Condensers 222 and 224 may be at two temperatures, e.g., 27° C. and −1° C. After the second condenser 224, the condensed liquid halogen may be directed toward halogen tank 214. The uncondensed gas from the second condenser 224 may be directed to water bath 216. The water/gas mixture may then be directed to stripper 218 with an alkane gas counterflow to strip additional halogen gas. The water may be recycled, and the alkane plus halogen gas mixture may pass over desiccant 226 to remove trace water vapor before being recirculated to halogenation reactor 210 for another cycle in the Alkene Formation Loop 200.

As water is a byproduct of the various reactions, the encapsulated metal oxide catalysts may need to be dehydrated between running of the two reaction loops. Accordingly, the system may include a dehydration gas. In some embodiments, the dehydration gas may be the alkane, which after passing over a desiccant (not shown) may be recirculated into the system for halogenation.

For continuous operation, there may preferably be a plurality of reactors containing the encapsulated metal oxide catalysts of the present invention such that each reactor may independently be in different stages of the process, e.g., one reactor participating in an Alkene Formation Loop and a second reactor participating in a Catalyst Regeneration and Halogen Gas Recovery Loop.

In some embodiments, a system for producing alkenes from alkanes according to a process of the present invention may be designed for production of various alkenes. For example, after halogenation of the alkane (or alternatively, from a provided alkyl halide feed gas), a system may have multiple flow paths through which to proceed. Each flow path may have a reactor with optionally different encapsulated metal oxide catalysts. If used simultaneously in a single system this may allow for flexibility in the system to produce different alkene products.

Figure 3:
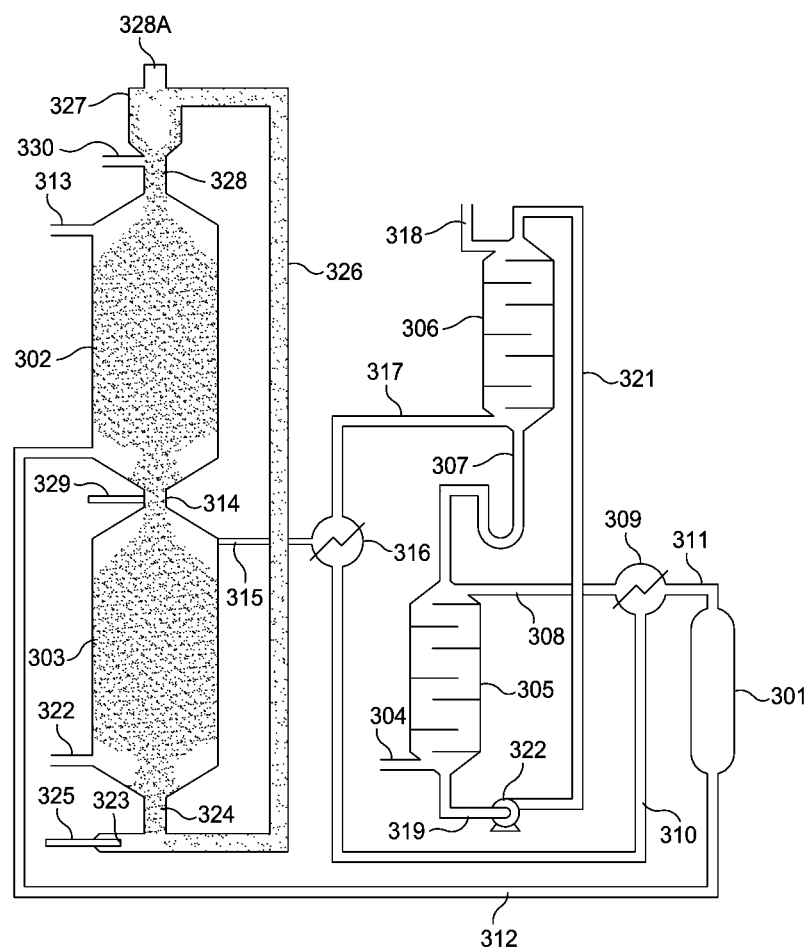
FIG. 3 is a schematic diagram of a nonlimiting example of a system of the present invention for producing alkenes according to some embodiments of the processes of the present invention.

Referring to FIG. 3, another nonlimiting example of a system of the present invention for producing alkenes, methane is fed through line 304 to stripper 305, stripping halide from halide solution coming down from stripper 306 through line 307. Methane with halide vapor from stripper 306 is led to saturation vessel 309 through line 308 where the balance of the required halide is added through line 310. The resulting mixture of methane and halide is fed through line 311 to reactor 301 where the balance of the required halide is added through line 310. The resulting mixture of methane and halide is fed through line 311 to reactor 301 where methyl halide and hydro-halide acid are produced. The methyl halide and hydro-halide acid are led through line 312 from reactor 301 to bottom of reactor 302 where they meet a countercurrent of magnesium base. The methyl halide, hydro-halide acid, and magnesium base react to form a product gas containing methanol, di-methyl ether, and ethylene, which are exhausted from reactor 302 through line 313. Metal halide formed in reactor 302 may be led by gravity or by vacuum to lower reactor 303 through line 314 where it meets a counter flow of oxygen or air forming halide, which together with excess oxygen or air are led through line 315 to cooler 316 where the condensed halide is led through line 310 to saturation vessel 309.

Line 317 leads excess oxygen or air to stripper 306 where it meets a countercurrent flow of solvent. In stripper 306 the halide is stripped from gases. The gases then leave stripper 306 through line 318 to exhaust to the atmosphere. Solvent loaded with halide flows downwardly through line 307 to stripper 305. Spent solvent is led through line 319 to a pump, which pumps solvent to stripper 306 through line 321. Oxygen or air is fed into reactor 303 through line 322. Magnesium base produced in reactor 303 is led to ejector 323 through line 324, which is fed with air through line 325 and conveys the magnesium base through line 326 to cyclone 327, which empties the basic magnesium through line 328 to reactor 302 and exhausts air to the atmosphere through line 328A. Steam through line 329 into line 314 prevents gases from reactor 302 to pass into reactor 303. Steam through line 330 prevents gases from cyclone 327 to pass into reactor 302.

Encapsulated metal oxide catalysts of the present invention for use in conjunction with a system as shown in FIG. 3 may have a higher crush strength and be substantially spherical.

To facilitate a better understanding of the present invention, the following examples of preferred or representative embodiments are given. In no way should the following examples be read to limit, or to define, the scope of the present invention.

EXAMPLES

Example 1

Highly porous encapsulated magnesium oxide catalysts of one embodiment of the present invention are made as follows: 50 parts by weight of fine powder magnesium stearate $Mg(C_{18}H_{35}O_2)_2$ are thoroughly mixed with 50 parts by weight of fine powder bentonite and enough water added to form a doughy mixture, which is then kneaded until smooth. The mixture is then pelletized and air dried at typical room temperatures. Once dried the pellets are calcined at a minimum temperature of 600° C. to form magnesium oxide encapsulated in a highly porous ceramic clay matrix, which is an example of an encapsulated metal oxide catalyst according to at least one embodiment of the present invention.

Highly porous encapsulated magnesium oxide can be made as follows: 50 parts by weight of fine powder magnesium citrate, $Mg(C_6H_5O_7)_2 \cdot 14H_2O$, are well mixed with 50 parts by weight of fine powder kaolin, 1 part by weight of ground X-type zeolite in the acid form and 50 parts by weight of water added to form a dough, which is then kneaded until smooth and then pelletized and dried. Once dried the pellets are calcined to at least about 600° C. to form the magnesium oxide encapsulated in a matrix of hard clay or porcelain. The proportions of magnesium citrate to clay can vary. The higher the proportion of clay, the harder the pellet, but the lower the capacity for halide or alcohol production, and thus, for alkene production. The pellets can be made spherical or in any other shape, by hand or machine, known in the art. Other types of clays and inorganic porous agglutinates, as are known in the art, may be used as the encapsulating material in embodiments of the present invention.

Example 2

A dough was produced by first producing a well-mixed dry mix of 75 g of bentonite powder and 125 g of magnesium carbonate tri-hydrate powder. Both powders were produced by forcing the materials through a fine sieve. Then 94.1 g of distilled water was added slowly while mixing. The dough was then hand pressed between two plastic sheets and cut into pellets having a size of about a 6 mm×6 mm×6 mm cube. The pellets were allowed to dry naturally, i.e., no added heat, overnight.

The dried pellets were then heated in air in a kiln with the following temperature profile to produce encapsulated metal oxide catalysts.

(1) Ramp to 250° C. over 40 minutes;
(2) ramp to 400° C. over 90 minutes;
(3) ramp to 600° C. over 40 minutes;
(4) hold at 600° C. for 30 minutes; and
(5) allow to cool slowly back to room temperature.

Figure 4:
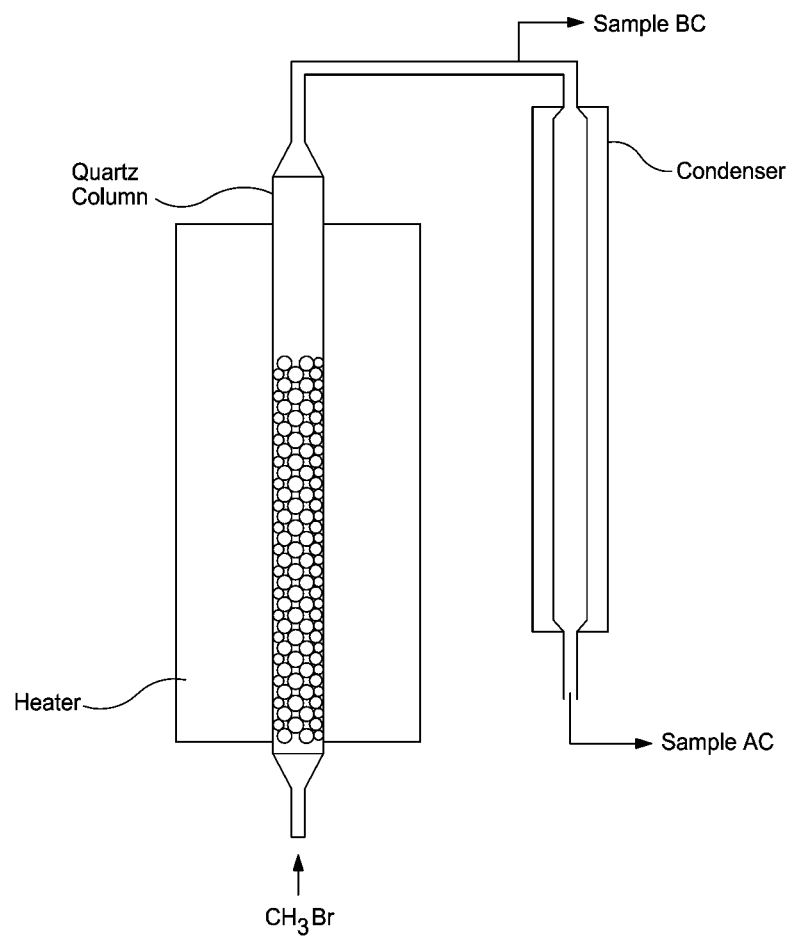
FIG. 4 is a schematic diagram of a nonlimiting example of a system of the present invention for producing alkenes according to some embodiments of the processes of the present invention.

The encapsulated metal oxide catalysts were then reacted with methyl bromide in the reactor illustrated in FIG. 4. Briefly, the encapsulated metal oxide catalysts were placed in a quartz column having a heater disposed thereabout. Methyl bromide was flowed from the bottom of the quartz column. The effluent at the top of the column was passed through a condenser. At different reaction temperatures, samples of the effluent were taken before and after the condenser ("BC" and "AC", respectively) and analyzed via gas chromatography, Table 1.

TABLE 1

| temp (° C.) | 280 | 280 | 300 | 300 | 337 | 337 |
|---|---|---|---|---|---|---|
| location | BC | AC | BC | AC | BC | AC |
| methane | 30.7% | 14.0% | 0% | 0% | 6.6% | 9.4% |
| ethylene | 69.3 | 86.0 | 100 | 100 | 93.4 | 90.6 |
| other | 0 | 0 | 0 | 0 | trace | trace |

Example 3

A dough was produced by first producing a well-mixed dry mix of 274.6 g of kaolin powder and 119.38 g of magnesium carbonate tri-hydrate powder. Both powders were produced by forcing the materials through a fine sieve. Then 300 mL of distilled water was added slowly while mixing. The dough was then hand pressed between two plastic sheets and cut into pellets having a size of about a 6 mm×6 mm×6 mm cube. The pellets were allowed to dry naturally, i.e., no added heat, for eleven days. The dried pellets were then calcined in air in a kiln to 1000° C. with a ramp time of about 5 hours.

The encapsulated metal oxide catalysts were then reacted with methyl bromide in the reactor illustrated in FIG. 4. The predominant product was butylene as determined by gas chromatography.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A method comprising:
   producing a dough comprising a clay, a metal organic salt, and water, wherein the metal organic salt is present in an amount of about 5% to about 50% of a metal of the metal organic salt by weight of the clay;
   forming a plurality of pellets from the dough;
   drying the pellets;
   calcining the pellets so as to form a plurality of encapsulated metal oxide catalysts that comprise a porous ceramic matrix and metal catalysts dispersed therein; and
   washing the encapsulated metal oxide catalysts with a water-miscible organic solvent, wherein the encapsulated metal oxide catalysts comprise a plurality of pores containing the metal catalysts having an average diameter of about 5 nm to about 300 nm.

2. The method of claim 1, wherein the clay comprises at least one selected from the group consisting of a pozzalonic material, kaolin, metakaolin, bentonite, bauxite, illite, vermiculite, Fuller's earth, hectorite, saponite, speiolite, shale, halloysite, pumice, pumicite, montmonillonite, a chlorite clay, a phylosilicate, mica, and any combination thereof.

3. The method of claim 1, wherein the metal organic salt comprises a salt of (1) a $C_1$-$C_{16}$ comprising at least one carboxylate and (2) any alkali, basic, or transition metal.

4. The method of claim 3, wherein the transition metal is magnesium or zinc.

5. The method of claim 1, wherein the dough further comprise at least one selected from the group consisting of an activation agent, a pore molding agent, and any combination thereof.

6. The method of claim 5, wherein the pore molding agent comprises at least one selected from the group consisting of glycol, diethylene glycol, glycerin, oligomers of ethylene glycol, malonic acid, succinic acid, and the like, or any combination thereof.

7. The method of claim 5, wherein the pore molding agent is present in an amount of about 1% to about 50% by weight of the clay.

8. The method of claim 1, wherein calcining involves heating to a temperature of about 600° C. to about 1000° C. in an oxygen-containing gas stream.

9. The method of claim 1, wherein the water-miscible organic solvent comprises at least one selected from the group consisting of acetone, an alcohol, and any combination thereof.

10. The of claim 1, wherein the encapsulated metal oxide catalysts comprise a plurality of pores between clay platelets having an average diameter of about 2 nm to about 50 nm.

11. The method of claim 1, wherein the encapsulated metal oxide catalysts have a void volume of about 25% to about 85%.

12. The method of claim 1, wherein the encapsulated metal oxide catalysts have a crush strength of about 10,000 psi or greater.

13. The method of claim 1, wherein the encapsulated metal oxide catalysts have a crush strength of about 60,000 psi or greater.

14. The method of claim 1, wherein the clay comprises bentonite and the metal organic salt comprises magnesium carbonate tri-hydrate.

15. The method of claim 1, wherein the clay comprises bentonite, wherein the metal organic salt comprises magnesium carbonate, and wherein the water-miscible organic solvent comprises methanol.

16. The method of claim 1, wherein the clay comprises kaolin and the metal organic salt comprises magnesium carbonate tri-hydrate, and wherein the dough further comprises an activation agent that comprises an X-type zeolite.

17. A method comprising:
producing a dough comprising a clay, a metal organic salt, and water, wherein the metal organic salt is present in an amount of about 5% to about 50% of a metal of the metal organic salt by weight of the clay;
forming a plurality of pellets from the dough;
drying the pellets;
calcining the pellets so as to form a plurality of encapsulated metal oxide catalysts that comprise a porous ceramic matrix and metal catalysts dispersed therein; and
washing the encapsulated metal oxide catalysts with a water-miscible organic solvent, wherein the encapsulated metal oxide catalysts have a void volume of about 25% to about 85%.

18. The method of claim 17, wherein the dough further comprise at least one selected from the group consisting of an activation agent, a pore molding agent, and any combination thereof.

19. The method of claim 18, wherein the pore molding agent comprises at least one selected from the group consisting of glycol, diethylene glycol, glycerin, oligomers of ethylene glycol, malonic acid, succinic acid, and the like, or any combination thereof.

20. The method of claim 18, wherein the pore molding agent is present in an amount of about 1% to about 50% by weight of the clay.

21. A method comprising:
producing a dough comprising a clay, a metal organic salt, and water, wherein the metal organic salt is present in an amount of about 5% to about 50% of a metal of the metal organic salt by weight of the clay;
forming a plurality of pellets from the dough;
drying the pellets;
calcining the pellets so as to form a plurality of encapsulated metal oxide catalysts that comprise a porous ceramic matrix and metal catalysts dispersed therein; and
washing the encapsulated metal oxide catalysts with a water-miscible organic solvent, wherein the encapsulated metal oxide catalysts have a crush strength of about 10,000 psi or greater.

\* \* \* \* \*